(12) United States Patent
Duftler et al.

(10) Patent No.: US 10,365,946 B2
(45) Date of Patent: *Jul. 30, 2019

(54) CLUSTERING BASED PROCESS DEVIATION DETECTION

(71) Applicant: INTERNATIONAL BUSINESS MACHINES CORPORATION, Armonk, NY (US)

(72) Inventors: Matthew J. Duftler, Mahopac, NY (US); Paul T. Keyser, Chicago, IL (US); Szabolcs Rozsnyai, New York, NY (US)

(73) Assignee: International Business Machines Corporation, Armonk, NY (US)

(*) Notice: Subject to any disclaimer, the term of this patent is extended or adjusted under 35 U.S.C. 154(b) by 408 days.

This patent is subject to a terminal disclaimer.

(21) Appl. No.: 14/030,652

(22) Filed: Sep. 18, 2013

(65) Prior Publication Data

US 2014/0297640 A1    Oct. 2, 2014

Related U.S. Application Data

(63) Continuation of application No. 13/851,618, filed on Mar. 27, 2013.

(51) Int. Cl.
  *G06F 9/46* (2006.01)
  *G16H 50/70* (2018.01)
  *G06F 11/34* (2006.01)

(52) U.S. Cl.
  CPC ............... *G06F 9/46* (2013.01); *G16H 50/70* (2018.01); *G06F 11/3452* (2013.01); *G06F 2201/86* (2013.01)

(58) Field of Classification Search
  CPC .... G06F 9/46; G06F 19/3443; G06F 11/3452; G06F 2201/86; G16H 50/70
  See application file for complete search history.

(56) References Cited

U.S. PATENT DOCUMENTS

| 7,676,384 B2 * | 3/2010 | Baker ................. G06F 17/3071 600/300 |
| 7,917,460 B2 * | 3/2011 | Talbot ................. G06K 9/6292 706/59 |
| 9,430,616 B2 * | 8/2016 | Duftler ................. G16H 40/20 |

(Continued)

FOREIGN PATENT DOCUMENTS

| JP | 2006228150 | 8/2006 |
| JP | 2012043113 | 1/2012 |

(Continued)

OTHER PUBLICATIONS

"DBSCAN"—Wikipedia, dated Jan. 25, 2012.*

(Continued)

*Primary Examiner* — Benjamin C Wu
(74) *Attorney, Agent, or Firm* — Tutunjian & Bitetto, P.C.; Rahan Uddin

(57) ABSTRACT

Systems and methods for data analysis include correlating event data to provide process instances. The process instances are clustered, using a processor, by representing the process instances as strings and determining distances between strings to form a plurality of clusters. One or more metrics are computed on the plurality of clusters to monitor deviation of the event data.

20 Claims, 3 Drawing Sheets

(56) References Cited

U.S. PATENT DOCUMENTS

| | | | |
|---|---|---|---|
| 10,181,012 B2* | 1/2019 | Duftler | G16H 40/20 |
| 2002/0022973 A1 | 2/2002 | Sun et al. | |
| 2003/0216939 A1 | 11/2003 | Bito et al. | |
| 2007/0136455 A1* | 6/2007 | Lee | G06F 21/564 |
| | | | 709/223 |
| 2008/0306894 A1* | 12/2008 | Rajkumar | G06Q 10/0637 |
| | | | 706/47 |
| 2009/0262131 A1* | 10/2009 | Suntinger et al. | 345/619 |
| 2009/0265288 A1* | 10/2009 | Chakravarty | G06N 5/022 |
| | | | 706/11 |
| 2010/0131253 A1 | 5/2010 | Benayon et al. | |
| 2010/0131434 A1 | 5/2010 | Magent et al. | |
| 2011/0166883 A1 | 7/2011 | Palmer et al. | |
| 2011/0185230 A1* | 7/2011 | Agrawal | G06F 11/0751 |
| | | | 714/26 |
| 2011/0271341 A1* | 11/2011 | Satish | G06F 21/552 |
| | | | 726/23 |
| 2011/0295773 A1* | 12/2011 | Fisher | G06Q 30/0631 |
| | | | 706/11 |
| 2012/0065987 A1 | 3/2012 | Farooq et al. | |
| 2012/0150498 A1 | 6/2012 | Shastri et al. | |
| 2012/0232926 A1 | 9/2012 | Boyle et al. | |
| 2012/0233000 A1* | 9/2012 | Fisher | G06Q 30/02 |
| | | | 705/14.71 |
| 2012/0253841 A1 | 10/2012 | Erlandsen et al. | |
| 2012/0290319 A1 | 11/2012 | Saria et al. | |
| 2013/0275149 A1 | 10/2013 | Gaines et al. | |
| 2013/0339060 A1 | 12/2013 | Delaney et al. | |
| 2014/0280075 A1* | 9/2014 | Huang et al. | 707/722 |
| 2015/0026808 A1* | 1/2015 | Perdisci | G06F 21/56 |
| | | | 726/23 |

FOREIGN PATENT DOCUMENTS

| | | |
|---|---|---|
| WO | WO0057264 A1 | 9/2000 |
| WO | WO2006132320 A1 | 8/2006 |

OTHER PUBLICATIONS

Non-Final Office Action for U.S. Appl. No. 13/851,675 dated Feb. 25, 2015.

Aalst, W. "Using Real Event Data to X-Ray Business Processes Helps Ensure Conformance Between Design and Reality" Communications of the ACM. vol. 55, No. 8. Aug. 2012. pp. 76-83.

Aiolli, F., et al. "Metric for Clustering Business Processes Based on Alpha Algorithm Relations" Department of Pure and Applied Mathematics, University of Padua, Italy. 2011. (pp. 1-17).

Bose, R., et al. "Context Aware Trace Clustering: Towards Improving Process Mining Results" Proceedings of the SIAM International Conference on Data Mining, SDM 2009. Apr./May 2009. pp. 401-412.

Cheng, H., et al. "Direct Discriminative Pattern Mining for Effective Classification" Proceedings of the 24th International Conference on Data Engineering, ICDE 2008. Apr. 2008. (10 Pages).

Ester, M., et al. "A Density-Based Algorithm for Discovering Clusters in Large Spatial Databases With Noise" Proceedings of 2nd International Conference on Knowledge Discovery and Data Mining. 1996. (6 Pages).

Greco, G., et al. "Mining Expressive Process Models by Clusteringworkflow Traces" Proceedings Advances in Knowledge Discovery and Data Mining, 8th Pacific-Asia Conference, PAKDD 2004. May 2004. pp. 52-62.

Hall, P., et al. "Choice of Neighbor Order in Nearest-Neighbor Classification" The Annals of Statistics. vol. 36, No. 5. 2008. pp. 2135-2152.

Hartmann, B., et al. "Review of Antibiotic Drug Use in a Surgical ICU: Management With a Patient Data Management System for Additional Outcome Analysis in Patients Staying More Than 24 Hours" Clinical Therapeutics. vol. 26, No. 6. Apr. 2004. pp. 915-924.

Huang, Z., et al. "On Mining Clinical Pathway Patterns From Medical Behaviors" Artificial Intelligence in Medicine. vol. 56, No. 1. Sep. 2012. pp. 1-16.

Jung, J., et al. "Workflow Clustering Method Based on Process Similarity" International Conference Computational Science and Its Applications—ICCSA 2006. May 2006. pp. 379-389.

Kastner, M., et al. "Heuristic Methods for Searching and Clustering Hierarchical Workflows" 12th International Conference Computer Aided Systems Theory—EUROCAST 2009. Feb. 2009. (8 Pages).

Lakshmanan, G., et al. "Leveraging Process Mining Techniques to Analyze Semi-Structured Processes" IT Professional. IEEE computer Society Digital Library. IEEE Computer Society. Aug. 2012. pp. 1-13.

Lo, D., et al. "Mining Closed Discriminative Dyadic Sequential Patterns" EDBT 2011, 14th International Conference on Extending Database Technology. Mar. 2011. pp. 1-12.

Qiao, M., et al. "Towards Efficient Business Process Clustering and Retrieval: Combining Language Modeling and Structure Matching" Business Process Management—9th International Conference, BPM 2011. Sep. 2011. pp. 199-214.

Rebuge, A., et al. "Business Process Anaylsis in Heathcare Environments: A Methodology Based on Process Mining" Information Systems. vol. 37, No. 2. Apr. 2012. pp. 1-18.

Sartipi, K., e al. "Mined-Knowledge and Decision Support Services in Electronic Health" International Workshop on Systems Development in SOA Environments, 2007. May 2007. (6 Pages).

Silva, V. et al. "Similarity-Based Workflow Clustering" Journal of Computational Interdisciplinary Sciences 2(1): 23-35. Jan. 2011. pp. 23-35.

Song, M., et al. "Trace Clustering in Process Mining" Business Process Management Workshops, BPM 2008 International Workshops. Sep. 2008. pp. 1-12.

Weijters, A., et al. "Process Mining With the Heuristicsminer Algorithm" Beta Working Paper Series, WP 166, Eindhoven University of Technology, Eindhoven, 2006.

Poelmans, J., et al., "Comgining business process and data discovery techniques for analyzing and improving integrated care pathways," Lecture Notes in Computer Science, vol. 6171, Jul. 2010. (pp. 1-14).

Non-Final Office Action for U.S. Appl. No. 13/851,755 dated Jun. 25, 2015.

Cavlan, O. et al., "Using Care Pathways to Improve Health Systems," Health International, Issue 11, Feb. 2011 (pp. 6-17).

Jacob, S.G. et al., "Data Mining in Clinical Data Sets: A Review," International Journal of Applied Information Systems, vol. 4, No. 6, Dec. 2012. (pp. 15-26).

Final Office Action for U.S. Appl. No. 13/851,755 dated Feb. 8, 2016.

\* cited by examiner

CLUSTERING BASED PROCESS DEVIATION DETECTION

CROSS-REFERENCE TO RELATED APPLICATIONS

This application is related to commonly assigned U.S. application Ser. No. 13/851,675, entitled "EXTRACTING KEY ACTION PATTERNS FROM PATIENT EVENT DATA," filed Mar. 27, 2013, and commonly assigned U.S. application Ser. No. 13/851,755, entitled "EXTRACTING CLINICAL CARE PATHWAYS CORRELATED WITH OUTCOMES," filed Mar. 27, 2013, both of which are incorporated herein by reference in their entirety.

This application is a Continuation application of co-pending U.S. patent application Ser. No. 13/851,618 filed on Mar. 27, 2013, incorporated herein by reference in its entirety.

BACKGROUND

Technical Field

The present invention relates to clustering, and more particularly to clustering based process deviation detection.

Description of the Related Art

In traditional Business Process Management environments, monitoring processes for deviations is based on defined process models. The process model indicates how activities and events can be carried out and which decisions (i.e., paths) can be made. Monitoring processes allows for the tracking of performance metrics (e.g., process cycle times, number of orders, costs, etc.). In such a managed environment, the behavior is known as it is specified in the process model. One could only track which defined paths are taken how often from a behavioral point of view.

In the area of semi-structured business processes, the process models are not specified in full detail in order to preserve a high degree of freedom. However, due to the lack of detailed process models, the task of monitoring processes is difficult.

SUMMARY

A method for data analysis includes correlating event data to provide process instances. The process instances are clustered, using a processor, by representing the process instances as strings and determining distances between strings to form a plurality of clusters. One or more metrics are computed on the plurality of clusters to monitor deviation of the event data.

A system for data analysis includes a correlation module configured to correlate event data stored on a computer readable storage medium to provide process instances. A clustering module is configured to cluster the process instances by representing the process instances as strings and determining distances between strings to form a plurality of clusters. A metric module is configured to compute one or more metrics on the plurality of clusters to monitor deviation of the event data.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
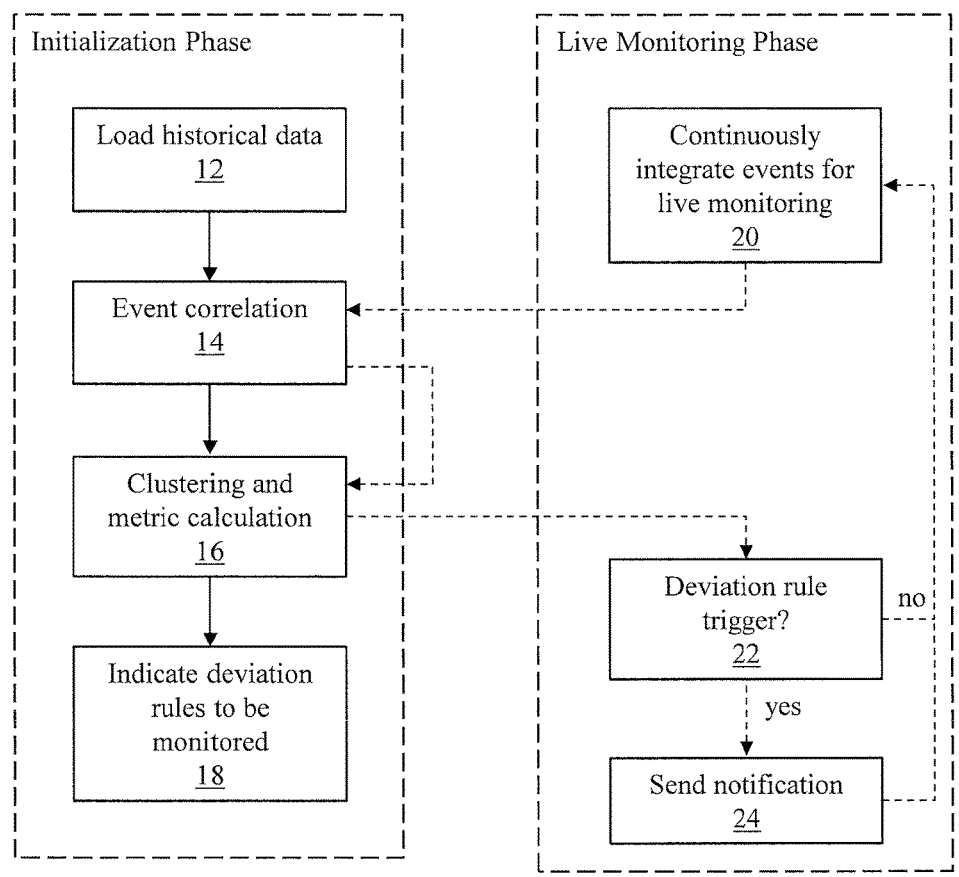
FIG. 1 shows a high-level diagram of clustering based process deviation detection, in accordance with one illustrative embodiment.

In accordance with the present principles, systems and methods are provided for clustering based process deviation detection. During an initialization phase, historical event data is correlated to form process instances. The historical event data preferably includes event attributes, such as, e.g., event type, timestamp, a key/value pair representation of the event payload, etc. Event data is correlated based on correlation rules using the event attributes. Groups of correlated events form process instances.

The process instances are clustered into a plurality of clusters. Clustering preferably includes transforming process instances into strings and determining, e.g., Levenshtein distances between strings. Process instances may be transformed into strings by mapping each event to a unique character (e.g., Unicode character) according to event type. Metrics are computed on the plurality of clusters, including, e.g., the distance between process instances, the distance between clusters and the size of clusters. Rules may be defined to monitor deviation on the data. Preferably, the rules are in the in-then form. The rules may reference individual clusters and metrics.

In a live monitoring phase, new event data are continuously integrated. The new event data are correlated with the historical event data, and clustering and metric calculation is performed. Deviation monitoring is achieved such that when a rule is triggered, an action is performed, which may include, e.g., sending a notification.

One advantage of the present principles is that process instances are input into a clustering method and the clusters are used for behavioral classification and behavioral deviation. The present principles enable proactive monitoring of process executions. Other advantages of the present principles include the detection of process deviations, the emergence of new behavioral patterns (e.g., growing clusters, shrinking clusters, new clusters, etc.), and the notification or trigger actions once a rule is triggered.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to FIG. 1, a high-level diagram of clustering based process deviation detection 10 is illustratively depicted in accordance with one illustrative embodiment. During an initialization phase, in block 12, historical data is loaded. The historical data preferably includes historical event data, including attributes for each event. In block 14, events are correlated, such that groups of correlated events form process instances. Event correlation may be performed based on user-specified correlation rules. In block 16, clustering of the process instances is performed and metrics are calculated. Clustering may include representing process instances as strings and determining the Levenshtein distance as a representation of process instance similarity. Metrics may be calculated as a distance between process instances, a distance between clusters, size of clusters, etc. Clusters may be analyzed for behavioral classification (e.g., good behavior, bad behavior, etc.) by user analysis, etc. In block 18, deviation rules may be indicated for monitoring. The rules may be in the if-then form to provide actions when a rule is triggered.

In a live monitoring phase, in block 20, new event data are continuously integrated. The new event data are correlated, along with the historical data, and clustering and metric calculation is performed. Live monitoring is performed, in block 22, by checking if a deviation rule is triggered. If a deviation rule is triggered, an action is performed. For example, an action may include, in block 24, sending a notification. The notification may indicate the behavior of clusters of data for live monitoring. This process is repeated to continuously integrate new event data.

Figure 2:
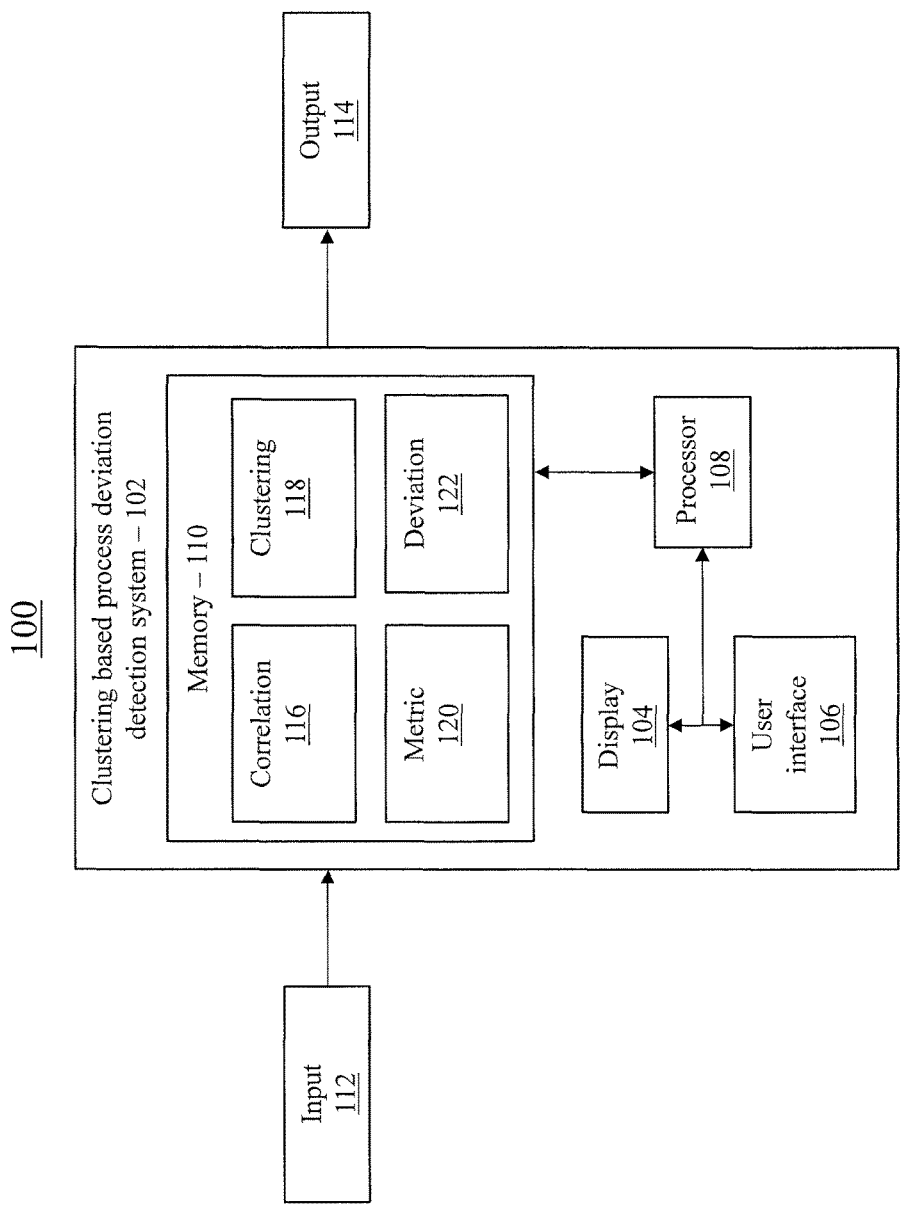
FIG. 2 is a block/flow diagram showing a system/method of clustering based process deviation detection, in accordance with one illustrative embodiment.

Referring now to FIG. 2, a block/flow diagram showing a system for clustering based process deviation detection 100 is illustrative depicted in accordance with one embodiment.

The system 100 detects clusters of behavior, segments them into, e.g., positive or negative behaviors, and monitors the evolution of behavior clusters based on a set of rules.

It should be understood that the present principles may be applied in a number of different applications. For example, the present principles will be discussed throughout this application with continued reference to examples relating to the healthcare field. However, it should be understood that the present principles are not so limited. Other applications may also be applied within the context of the present principles, such as, e.g., the insurance field.

The system 100 may include a system or workstation 102. The system 102 preferably includes one or more processors 110 and memory 112 for storing event data, applications, modules and other data. The system 102 may also include one or more displays 104 for viewing. The displays 104 may permit a user to interact with the system 102 and its components and functions. This may be further facilitated by a user interface 106, which may include a mouse, joystick, or any other peripheral or control to permit user interaction with the system 102 and/or its devices. It should be understood that the components and functions of the system 102 may be integrated into one or more systems or workstations.

The system 102 may receive input 112, which may include, e.g., historical event data. The historical event data includes events representing activities of processes. In one example, the events include medical events, such as, e.g., medications, labs, diagnoses, vital signs, etc. for a cohort of patients. Other types of events may also be employed. Events are stored in memory 110, and transformed according to the target event schema such that each event includes event attributes, such as, e.g., event type, timestamp, key/value pair representation of the event payload, etc.

Example 1 illustrates an event with event attributes. The event AddSWIFTLink includes the event type AddSWIFTLink, the timestamp 1319570460000, and workflow ID 902. Events may include other types of attributes as well.

EXAMPLE 1

The event AddSWIFTLink is shown including event attributes.

```
<AddSWIFTLink>
    <eventtype>AddSWIFTLink</eventtype>
    <timeStamp>1319570460000</timeStamp>
    <workflowId>902</workflowId>
    ...
</AddSWIFTLink>
```

Correlation module 116 is configured to correlate the events, such that correlated events are grouped to form process instances (also referred to as "traces" or "cases"). Events are correlated based upon correlation rules that indicate how events are related. The correlation rules are preferably provided by a user by input 112. This may involve, e.g., display 104 and/or user interface 106. The groups of correlated events form process instances. In one example, a correlation rule indicates that events are related where: EventTypeX.AttributeA=EventTypeY.AttributeB.

Example 2 illustrates correlations rules in the healthcare context. Correlation rules may be provided to correlate medical events having an attribute indicating the same patient. The correlation rule in Example 2 indicates that events of the type Vitals correlate with events of the type LabTest if the values of the attribute patientId for each event are equal.

EXAMPLE 2

An exemplary correlation rule in the healthcare context.
Vitals.patientId=LabTest.patientId Clustering module 118 is configured to identify clusters of process instances. Process instances are first transformed to a string-based representation. In one embodiment, string-based representations are formed based on the event type names. Specifically, string-based representations are formed by mapping each event type to a unique character (e.g., Unicode characters). The order of the resulting string corresponds to the ordering of the process instances (e.g., chronologically). Other approaches for string-based transformations are also contemplated.

In one example, event types are mapped to a unique character. For example, Vitals=A; LabTest=B; Diagnoses=C. Traces can be transformed into a string-based representation using the mapped characters. Table 1 shows the transformation of exemplary process traces into string-based representations.

TABLE 1 exemplary transformation of process instance traces into string-based representations.

| Trace | String |
| --- | --- |
| Vitals → Vitals → Vitals → LabTest → Diagnosis | AAABC |
| Vitals → LabTest → Vitals → Vitals → Diagnosis | ABAAC |
| Vitals → Vitals → LabTest → Diagnosis → Vitals | AABCA |

The string-based representations may be grouped into clusters using, e.g., a density-based clustering based on the Levenshtein distance (i.e., string edit distance) metric to determine relationships between process instances. Density-based clustering may include, e.g., DBSCAN (density-based spatial clustering of applications with noise), etc. Other forms of clustering and/or metrics may also be employed.

The Levenshtein distance measures the string edit distance between two sequences. The string edit distance between two strings represents the minimum number of single-character edit operations to transform one string into the other. Edit operations may include, e.g., insertion, deletion and substitution. The Levenshtein distance is a good measure of similarity for determining process instance similarity. Density-based clustering using the Levenshtein distance metric forms clusters of process instances that are similar.

Metric module 120 is configured to compute metrics on the clusters of process instances. The metrics may be used to determine behavioral classification and behavioral deviation. In one embodiment, a first metric includes the distance between individual process instances. A Levenshtein distance may be computed between string-based representations of two process instances. In another embodiment, a second metric includes the distance between each of the clusters. A Levenshtein distance may be computed for the average of pairwise proximity between process instances in two clusters. In more detail, the average Levenshtein distance between all combinations of traces within a cluster is computed for two clusters. The difference the average distances provides the second metric. In yet another embodiment, a third metric includes the size of each cluster. The size of a cluster is represented as the number of process instances in a cluster. The size of each cluster represents its significance. It should be understood that other metrics and other distance metrics may also be employed within the scope of the present principles.

Clusters are analyzed for behavior classification to, for example, classify clusters having good behavior and clusters having bad behavior. This may include, e.g., user analysis through human reasoning, etc. Deviation module 122 monitors metrics of clusters based on deviation rules for behavioral analysis of the clusters.

Deviation module 122 is configured to perform different actions when a deviation rule is triggered. The deviation rules may be specified by a user by input 112. This may involve, e.g., display 104 and/or user interface 106. Preferably, rules are in the if-then form: "if <condition>, then <action>." The <condition> field allows reference to individual clusters and metrics. Other rule formats may also be employed. For example, rules may be in the forms of if-then-else expressions, switch statements, etc.

EXAMPLE 3

Illustrative deviation rules.

```
IF Cluster("GoodBehavior").size( ) < Cluster("BadBehavior").size( )
    THEN SendNotificatoin("Bad Behaviors are developing")
IF distance(Cluster("GoodBehavior"), Cluster("BadBehavior"), Now( )) >
    distance(Cluster("GoodBehavior"), Cluster("BadBehavior"),
    LastMonth( ))
    THEN SendNotification("...")
IF Clusters(Now( )).diff(
    Clusters(diff(ClusterList(LastMonth( ))) AND
    Clusters(Now( )).size( ) > Clusters(LastMonth( )).size( )
    THEN SendNotification("New Behavior discovered")
```

In a live monitoring phase of system 102, new events may be loaded into the system 102 in a continuous manner. New events are received as input 112 and stored in memory 110 in accordance with the target event schema, such that each event includes attributes indicating event type, timestamp, a key/value pair representation of the event payload, etc. New events are correlated with existing events by correlation module 116, clustered in clustering module 118, and metrics are computed in metric module 120. Deviation module 122 monitors the conditions of deviations rules as new events are continuously integrated into the system 102. For each triggering rule, the indicated action is performed. This may involve, for example, sending notifications that certain clusters are growing or shrinking, new clusters are forming, etc. Clusters that are classified, e.g., as having good behavior or bad behavior may then provide for behavioral analysis to monitor conditions of clusters based on behaviors. Other actions or notifications may also be employed. Actions of the triggering rules may be provided as an output 114, which may include, e.g., notifications, metrics, action results of a rule, etc.

One advantage of the present principles is that process instances are clustered such that the clusters can be used for behavioral classification and behavioral deviation. The present principles may provide for rules that may be setup to monitor process deviations, monitor the emergence of new behavioral patterns, such as, e.g., growing clusters, shrinking clusters, new clusters, etc., and send notifications or trigger actions once a rule is triggered.

Figure 3:
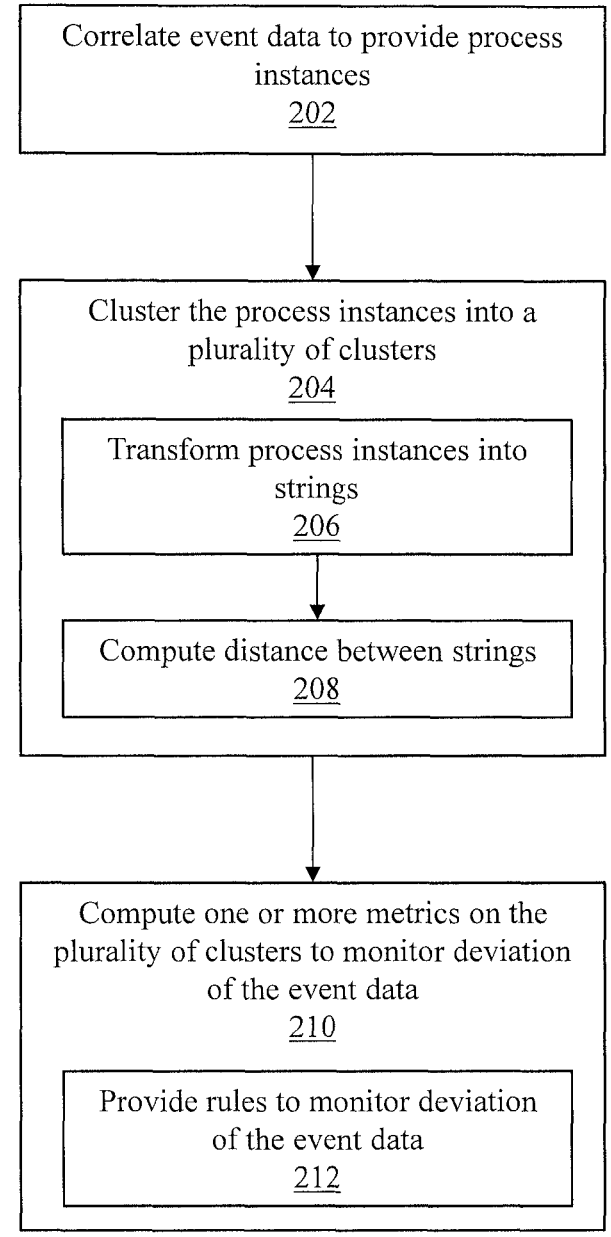
FIG. 3 is a block/flow diagram showing a system/method of clustering based process deviation detection, in accordance with one illustrative embodiment.

Referring now to FIG. 3, a block/flow diagram showing a method for clustering based process deviation detection 200 is illustratively depicted in accordance with one embodiment. In block 202, event data are correlated into process instances. The event data may include historical event data in an initialization phase. In a live monitoring phase, the event data may include new event data. The event data include events having event attributes indicating, e.g., event type, timestamp, key/value pair representation of the event payload, etc. Events are preferably correlated based upon correlation rules, which may be specified by a user. The groups of correlated events form process instances.

In block 204, the process instances are clustered into a plurality of clusters. In block 206, process instances are transformed into strings. Preferably, events are mapped to unique characters based on event type. The order of the string corresponds to the order events in the process instances. The process instances are clustered, in block 208, by computing the distance between strings. Preferably, the distance includes the Levenshtein distance; however other metrics are also contemplated. Clustering may include density-based clustering, such as, e.g., DBSCAN, etc. to provide a plurality of clusters. The plurality of clusters may be analyzed for behavioral classification (e.g., good behavior, bad behavior, etc.), which may involve user analysis for human reasoning.

In block 210, the plurality of clusters is monitored using rules based on metrics of the plurality of clusters. Metrics may include the distance between process instances as the Levenshtein distance between the string-based representations of the process instances. Metrics may also include the distance between clusters as the average pairwise proximity between process instances of the clusters using the Levenshtein distance. Metrics may further include the size of the cluster as the number of process instances in the cluster. Other forms of metrics may also be employed.

In block 212, rules are provided to monitor deviation in the event data. The rules may indicate actions that are performed when a rule is triggered. Preferably, the rules are in the if-then form: "if <conditions>, then <actions>." The <conditions> field allows for reference to individual clusters and metrics to provide behavior deviation monitoring. The action may include a send notification command that sends a notification to a user that, e.g., a clustering is growing or shrinking, a new cluster is forming, etc. By applying behavioral analysis on the clusters, e.g., to identify clusters having good behaviors and bad behaviors, behavioral deviation can be performed to identify whether good behavior clusters are growing, bad behavioral clusters are shrinking, etc.

Having described preferred embodiments of a system and method for clustering based process deviation detection (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A non-transitory computer readable storage medium comprising a computer readable program for improving behavioral attributes of clusters generated in a healthcare environment including a plurality of patients by removing clusters exhibiting bad behaviors, wherein the non-transitory computer readable program when executed on a computer causes the computer to perform the steps of:

in an initialization phase:
  correlating, by a correlation module, medical event data having attributes indicating a common patient, the medical event data stored in a medical event data database to create process instances, the correlation based on user-specified correlation rules;
  clustering, by a clustering module, the process instances by representing the process instances as strings and determining distances between strings to form a plurality of clusters;
  computing, by a processor and a memory, one or more metrics based on the plurality of clusters to determine behavioral classification and behavioral deviation of the medical event data stored in the medical event data database, the behavioral deviation based on user-specified deviation rules prompting predetermined user-defined actions in response to the user-specified deviation rules being triggered, the predetermined user-defined actions indicating a behavior of clusters of data;
in a live monitoring phase:
  collecting new medical event data in the medical event data database and comparing the new medical event data with prior medical event data to create new process instances;
  clustering the new process instances by representing the new process instances as strings and determining distances between strings to form a plurality of new clusters;
  detecting, by the processor and the memory, new behavior patterns of the clusters, wherein each of the new behavior patterns is determined by comparing current cluster data with old cluster data to create the plurality of new clusters with new behavior patterns;
  incorporating the new behavior patterns of the clusters to the behavioral classification and behavioral deviation of the medical event data stored in the medical event data database to define more comprehensive medical-related clusters free of bad behaviors by applying new user-specified correlation and deviation rules created based on the incorporated new behavioral patterns;
  notifying a user, via a notification, when the new behavior patterns are created and what specific behaviors of the plurality of new clusters are exhibited during the live monitoring phase; and
  transforming the medical event data according to a target schema, causing the transformed medical event data to include attributes selected from the group consisting of an event type, a timestamp, and a key/value pair representation of an event payload.

2. The computer readable storage medium as recited in claim 1, wherein representing the process instances as strings includes mapping events of the medical event data to unique characters according to event type.

3. The computer readable storage medium as recited in claim 1, wherein the string representation includes event type names.

4. The computer readable storage medium as recited in claim 1, wherein the string representation has an order corresponding to a sequence of execution in a process instance.

5. The computer readable storage medium as recited in claim 1, wherein the medical event data is historical data representing activities of processes.

6. The computer readable storage medium as recited in claim 1, wherein the user-specified deviation rules are defined in a "if-then" format.

7. The computer readable storage medium as recited in claim 1, wherein the behavioral classification includes distinguishing between good behavior and bad behavior.

8. The computer readable storage medium as recited in claim 1, wherein the clustering uses density-based spatial clustering of applications with noise.

9. A system for improving behavioral attributes of clusters generated in a healthcare environment including a plurality of patients by removing clusters exhibiting bad behaviors, the system comprising:
  at least one of a display device and a user interface; and
  a processor and a memory, the processor and the memory configured to:
    in an initialization phase:
      correlate, by a correlation module, medical event data having attributes indicating a common patient, the medical event data stored in a medical event data database to create process instances, the correlation based on user-specified correlation rules;
      cluster, by a clustering module, the process instances by representing the process instances as strings and determining distances between strings to form a plurality of clusters;
      compute, by a processor and a memory, one or more metrics based on the plurality of clusters to determine behavioral classification and behavioral deviation of the medical event data stored in the medical event data database, the behavioral deviation based on user-specified deviation rules prompting predetermined user-defined actions in response to the user-specified deviation rules being triggered, the predetermined user-defined actions indicating a behavior of clusters of data;
    in a live monitoring phase:
      collect new medical event data in the medical event data database and comparing the new medical event data with prior medical event data to create new process instances;
      cluster the new process instances by representing the new process instances as strings and determining distances between strings to form a plurality of new clusters;
      detect, by the processor and the memory, new behavior patterns of the clusters, wherein each of the new behavior patterns is determined by comparing current cluster data with old cluster data to create the plurality of new clusters with new behavior patterns;
      incorporate the new behavior patterns of the clusters to the behavioral classification and behavioral deviation of the medical event data stored in the medical event data database to define more comprehensive medical-related clusters free of bad behaviors by applying new user-specified correlation and deviation rules created based on the incorporated new behavioral patterns;
      notify a user, via a notification, when the new behavior patterns are created and what specific behaviors of the plurality of new clusters are exhibited during the live monitoring phase; and
      transform the medical event data according to a target schema, causing the transformed medical event data to include attributes selected from the group consisting of an event type, a timestamp, and a key/value pair representation of an event payload.

10. The system as recited in claim 9, wherein the processor and the memory are further configured to map events of the medical event data to unique characters according to event type.

11. The system as recited in claim 9, wherein the processor and the memory are further configured to compute at least one of a distance between process instances, a distance between clusters, and a size of a cluster.

12. The system as recited in claim 9, wherein the string representation includes event type names.

13. The system as recited in claim 9, wherein the string representation has an order corresponding to a sequence of execution in a process instance.

14. The system as recited in claim 9, wherein the medical event data is historical data representing activities of processes.

15. The system as recited in claim 9, wherein the user-specified deviation rules are defined in a "if-then" format.

16. The system as recited in claim 9, wherein the processor and the memory are further configured to create the user-specified correlation rules to identify correlated events as process instances.

17. The system as recited in claim 9, wherein the clustering module is further configured to determine Levenshtein distances.

18. The system as recited claim 9, wherein the user is notified by using at least one of a display and a user interface.

19. The system as recited in claim 9, wherein the behavioral classification includes distinguishing between good behavior and bad behavior.

20. The system as recited in claim 9, wherein the clustering uses density-based spatial clustering of applications with noise.

* * * * *